(12) United States Patent
Augstein et al.

(10) Patent No.: US 9,638,655 B2
(45) Date of Patent: *May 2, 2017

(54) TEST ELEMENT ANALYSIS SYSTEM WITH CONTACT SURFACES COATED WITH HARD MATERIAL

(71) Applicant: Roche Diagnostics Operations, inc., Indianapolis, IN (US)

(72) Inventors: Manfred Augstein, Mannheim (DE); Joerg Dreibholz, Altrip (DE); Stefan Riebel, Ludwigshafen-Edigheim (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 199 days.

This patent is subject to a terminal disclaimer.

(21) Appl. No.: 14/167,344

(22) Filed: Jan. 29, 2014

(65) Prior Publication Data

US 2014/0147913 A1 May 29, 2014

Related U.S. Application Data

(63) Continuation of application No. 11/507,327, filed on Aug. 21, 2006, now Pat. No. 8,673,213, which is a (Continued)

(30) Foreign Application Priority Data

Mar. 10, 2004 (DE) .......................... 10 2004 011 648

(51) Int. Cl.
   *G01N 27/26* (2006.01)
   *G01N 33/487* (2006.01)

(52) U.S. Cl.
   CPC .......... *G01N 27/26* (2013.01); *G01N 33/4875* (2013.01)

(58) Field of Classification Search
   CPC ........................... G01N 27/26; G01N 33/4875
   See application file for complete search history.

(56) References Cited

U.S. PATENT DOCUMENTS

| 4,405,849 A | 9/1983 | Frame |
| 4,680,438 A * | 7/1987 | Witting et al. ............... 200/268 |

(Continued)

FOREIGN PATENT DOCUMENTS

| DE | 4305058 | 8/1994 | |
| DE | 10222271 | * 6/2003 | ............... C23C 4/00 |

(Continued)

OTHER PUBLICATIONS

Goetz et al., Translation of DE10222271, 2003, p. 1-4.*

(Continued)

*Primary Examiner* — Lore Jarrett
(74) *Attorney, Agent, or Firm* — McDonnell Boehnen Hulbert & Berghoff LLP

(57) ABSTRACT

The invention concerns a test element analytical system for the analytical examination of a sample, especially a body fluid, comprising at least one test element with one or more measuring zones and contact areas located on the test element, in particular electrodes or conductor paths, the sample to be examined being brought into the measuring zone to carry out an analysis in order to determine a characteristic measured quantity for the analysis, and an evaluation instrument with a test element holder for positioning the test element in a measuring position and a measuring device for measuring the characteristic change, the test element holder containing contact elements with contact areas which enable an electrical contact between the contact areas of the test element and the contact areas of the test element holder, characterized in that one of these contact areas is provided with an electrically conductive hard material surface.

12 Claims, 3 Drawing Sheets

Related U.S. Application Data continuation of application No. PCT/EP2005/002397, filed on Mar. 8, 2005.

(56) References Cited

U.S. PATENT DOCUMENTS

| | | | |
|---|---|---|---|
| 5,017,264 | A | 5/1991 | Yamazaki et al. |
| 5,160,278 | A | 11/1992 | Johnson |
| 5,282,950 | A | 2/1994 | Dietze et al. |
| 5,351,396 | A | 10/1994 | Sawada et al. |
| 5,409,762 | A | 4/1995 | Ozaki et al. |
| 5,855,951 | A | 1/1999 | Nelson et al. |
| 5,858,802 | A * | 1/1999 | Chai-Gao et al. ............ 436/524 |
| 6,007,390 | A | 12/1999 | Cheng et al. |
| 6,029,344 | A | 2/2000 | Khandros et al. |
| 6,046,051 | A | 4/2000 | Jina |
| 6,134,461 | A | 10/2000 | Say et al. |
| 2002/0157948 | A2 | 10/2002 | Liamos et al. |
| 2003/0102213 | A1 * | 6/2003 | Gotoh et al. ................ 204/400 |
| 2003/0187338 | A1 | 10/2003 | Say et al. |
| 2004/0115994 | A1 | 6/2004 | Wulff et al. |
| 2006/0052682 | A1 | 3/2006 | Joseph et al. |
| 2007/0249921 | A1 | 10/2007 | Groll et al. |
| 2011/0186428 | A1 * | 8/2011 | Beaty .................. G01N 27/327 204/403.01 |

FOREIGN PATENT DOCUMENTS

| | | |
|---|---|---|
| EP | 0074630 | 3/1983 |
| EP | 0082070 | 6/1983 |
| GB | 2130795 | 6/1984 |
| GB | 2145523 A | 3/1985 |
| JP | 02-266255 | 10/1990 |
| JP | 3162660 | 7/1991 |
| JP | 08-075820 | 3/1996 |
| JP | 2855718 | 11/1998 |
| JP | 2855718 | 2/1999 |
| JP | 2000-299150 | 10/2000 |
| JP | 2001-311712 | 11/2001 |

OTHER PUBLICATIONS

Shigeki, et al., Connecting Device, 2000, Mitsubishi, Computer Translation of Detained Description of the Invention of JP Pub. No. 2000-299150.

MacMillan Dictionary, synonynms or related words for metals, www.macmillandictionary.com, printed on Sep. 18, 2013.

Longman English Dictionary Online, definition of bronze, www.idoceonline.com, printed on Sep. 18, 2013.

Declaration of Matthew S. Simmons, dated Nov. 5, 2013.

Roempp Lexikon der Chemie, 2005, Harstoffe, Fachgebiet Chemie, Unterthema Metalurgie (concise summary in paragraph [0028] of the specification).

English language translation of Office Action for Japanese Patent Application No. 2007-502256.

* cited by examiner

TEST ELEMENT ANALYSIS SYSTEM WITH CONTACT SURFACES COATED WITH HARD MATERIAL

CROSS-REFERENCE TO RELATED APPLICATIONS

This application is a continuation of U.S. application Ser. No. 11/507,327, filed Aug. 21, 2006, now U.S. Pat. No. 8,673,213, which is a continuation of International Application No. PCT/EP2005/002397, filed Mar. 8, 2005, which claims priority to German Application 10 2004 011 648.2 filed Mar. 10, 2004.

BACKGROUND OF THE INVENTION

The invention concerns a test element analytical system for the analytical examination of a sample and in particular a body fluid of humans or animals. The system comprises at least two components, i.e., a test element which has a measuring zone into which the sample to be examined is moved in order to carry out an analysis in order to measure a measurable variable that is characteristic for the analysis, and an evaluation device with a test element holder in order to position the test element in a measuring position in order to carry out the measurement and a measuring device for measuring the characteristic measurable variable.

Test element analytical systems are commonly used especially in medical diagnostics for analysing body fluids such as blood or urine. The sample to be examined is firstly applied to a test element. Here the process steps that are required to detect the analyte which are usually chemical, biochemical, biological or immunological detection reactions or physical interactions take place which result in a characteristic and measurable change of the test element especially in the area of the measuring zone. In order to determine this characteristic change the test element is inserted into an evaluation device which determines the characteristic change of the test element and provides it in the form of a measured value for display or further processing.

Test elements are often designed as test strips which are essentially composed of an elongate support layer, usually made of a plastic material, and a measuring zone with a detection layer containing detection reagents and, if necessary, other auxiliary layers such as filtration layers. The test elements of the present invention additionally contain contact areas which can be used to make an electrical contact between the test element and the evaluation device. In the case of electrochemical assay methods conductor paths and electrodes are mounted on the test element. Even test elements which do not use methods of electrochemical analysis can have electrically conducting contact areas for example in order to transfer calibration data or batch information that are stored on the test element to the evaluation instrument.

The accompanying evaluation devices have test element holders with special contact elements which make an electrically conducting contact between the test element and the measuring and evaluation electronics of the evaluation instrument. These contact elements are usually in the form of electrical plug connections with metallic spring elements which are often provided with a noble metal surface usually of gold or platinum. The test strips are inserted into the test element holder for the measurement during which the contact areas of the contact elements are moved across the electrodes of the test elements. In an end position the contact area of the contact elements of the evaluation instrument are then in contact with the contact area of the test element. An electrically conducting connection is made between the test element and evaluation instrument by a pressing force that is in particular defined by the shape and spring force of the contact element. This should in particular ensure that the transition resistance between the contact area of the contact element of the evaluation instrument and the contact area of the test element is as low and constant as possible to enable an exact and reproducible signal transfer. A constant and reproducible transition resistance is especially important in order to still obtain exact measurement results even after a test element has previously been plugged in many times and thus to obtain a high and reproducible measurement accuracy especially with regard to the fact that such test element analytical systems are often used for many years or many tens of thousands of plugging operations are carried out. This is of major importance especially in the clinical field where such test systems often have to handle a high throughput.

A major advantage of pluggable contact devices is the ability to easily join and separate the electrical connection so that the test element and evaluation device can be stored and used independently of one another. Since the contact areas should, on the one hand, ensure that the transfer of electrical current is as optimal as possible which requires a certain contact pressure, but, on the other hand, joining the contact connection and in particular repeated joining and separating the contact connection puts a great strain on the connection, the contact areas are often provided with a layer of noble metal for example by plating or galvanizing with gold, silver, platinum or palladium. The often high mechanical strain on the contact areas especially due to abrasion, deposition or scratching of the contact areas is thus also a problem because a certain contact pressure has to be ensured for a reliable electrical contact and a certain insertion path of the test element is necessary for mechanical reasons and in particular to ensure guidance when plugging in and mechanical stability in the plugged state. It is very important that the contact areas are as resistant as possible to external influences in order to make a very secure contact between the contact areas of an electrical contact connection and with regard to having the lowest possible contact resistances. In this connection the external influences can be of a chemical, physical or mechanical type. Thus, especially during the plugging process, the two contact areas rub against one another resulting in a very high mechanical strain. Corrosion effects and especially crevice corrosion also have an adverse effect on the contact security and contact resistance. Another problem of such test element analytical instruments is that the support material of the test elements that are used often consists of an elastic and relatively soft plastic foil on which the contact areas and electrodes are mounted so that this structure on a relatively soft base material can have disadvantages for an exact contacting.

A major disadvantage of noble metal-noble metal pairs for contact areas of such plug-in connections is that, even irrespective of their geometry and/or the pressing force, the metal surfaces are very often damaged when the contact areas are joined and thus electrical contact problems occur. Such contact problems often manifest themselves in that the transition resistances between the plug and contact element become very high or in an extreme case there may be no longer any electrical contact between the components of the contact connection. When observed under the microscope the picture of damage that often results, especially in the case of flat contacts such as conductor paths or electrodes, is characterized by a major change in the thickness of the metal layer of these contact areas after the insertion. Thus the metal layer of the electrodes is strongly deformed in some areas by the second contact area that moves across it, in particular in the form of grooves, ridges and scratches. This pattern of damage occurs especially when the electrodes are mounted on relatively soft base materials. These deformations may become so large that the metal layer is completely stripped away in some areas by the second contact area moving across it. In this case electrical contact between the test element and evaluation instrument is no longer possible. Such deformations of metal layers which serve as contact areas manifest themselves as non-defined and considerably increased transition resistances or in the complete lack of an electrical contact. Such contact elements are therefore unsuitable for use in analytical systems which are intended to ensure a reproducible determination of analyte over a long period of use.

Hence in order to overcome these disadvantages the following solutions have been given in the prior art:

In order to ensure a very secure contact of plug-in connections especially under high mechanical and/or chemical stress, DE 102 22 271 A1 describes a method for increasing the mechanical and/or chemical resistance of an electrical contact connection between two contact parts by coating at least one of the contact parts with the aid of a thermal spraying process in the area of the contact areas. The aim of this application is to minimize the wear of the contact area by this coating. It mentions plug-in connections of electronic components such as conductor boards and printed circuit boards, or sliding contacts for example in motors as fields of applications for such contact connections. Such contact connections are especially characterized in that after the involved contact areas have been contacted once, the contact connection is subjected to a continuously high mechanical strain for example by vibrations or continual grinding together of the contact areas resulting in a large amount of wear of the involved contact areas in this area. The object of this application is in particular to minimize the wear on the contact areas themselves rather than to ensure a reliable electrical contact of the contact areas even after multiple joining and separation of the contact connection. Hard-wearing metal alloys such as bronze are mentioned as coating materials which are applied to one or both contact areas in order to thus reduce the wear on these contact areas themselves. The coating itself is carried out using thermal spraying processes. Such processes which use high temperatures are unsuitable for test elements whose test supports are very often composed of thin plastic foils since such plastic foils do not have the necessary heat resistance. The layer thickness of the coating layer has to be relatively large at 10 µm to 200 µm in order to enable a durable connection even under high strain and to enable the still unavoidable wear. Such increased wear phenomena occur in particular when both contact areas are provided with such a hard-wearing coating.

The European Patent Application EP 0 082 070 also describes a process for protecting electrical contact connections especially in switches and relays. The aim of this application is to protect metals and especially metal contacts from wear by coating. Like DE 102 22 271 A1 the coating should make the contact areas more resistant to wear. For this purpose a layer of titanium nitride is applied to the existing metal contacts which is characterized by the following features: an adhesion of more than 180 kg/cm$^2$, high chemical resistance, high abrasion resistance and a specific resistance of ca. 500 µΩ*cm. Also in this case the coating is used to minimize the wear of the contact areas themselves rather than to ensure a reliable electrical contact of the contact areas even after multiple joining and separation of the contact connection.

U.S. Pat. No. 6,029,344 describes spring contact elements especially for electrically contacting electronic components which are coated with a hard material. The aim is to modify the mechanical properties of the contact connection by the coating of the hard material. This is especially intended to improve the elastic properties of the contact element. In this case the coat is not used primarily to reduce the wear of the contact areas or to make a more secure contact, but rather to modify the elastic properties of the spring contacts. For this purpose the spring contacts made of relatively soft base materials such as gold are coated with a material which has a higher yield strength than the base material at least in the areas that are shaped in such a manner that they allow a spring action of the contact element. Examples of such materials that are mentioned are in particular metals such as nickel, copper, cobalt, iron, gold, silver, elements of the platinum group and other noble metals, semi-noble metals, tungsten, molybdenum, tin, lead, bismuth and indium and alloys thereof. These materials are referred to as hard materials in the sense of U.S. Pat. No. 6,029,344 and are defined as materials which have a yield strength of greater than 80,000 psi. Hard materials are defined completely differently in the sense of the present application. Such hard materials according to U.S. Pat. No. 6,029,344 are not suitable for ensuring the requirements with regard to a very high abrasion resistance and high contact reliability even for multiple insertions but rather serve to improve the elastic properties of the spring contact. The layer thicknesses of the hard material coating have to be between ca. 6 and 125 µm and have to be at least one fifth to five-fold the layer thickness of the base material of the spring contacts according to U.S. Pat. No. 6,029,344 in order to improve the mechanical and in particular the elastic properties of the contact element.

The documents described above describe processes for coating surfaces of electrical contact elements which either serve to reduce the abrasion and the wear of the contact areas themselves or to improve the elastic properties of the contact element. A fundamental problem which cannot be satisfactorily solved by the aforementioned processes and devices is to ensure a reliable and defined electrical connection between the contact areas of a contact element over a long time period especially under high mechanical strain and even after numerous contacting operations.

SUMMARY OF THE INVENTION

It is against the above background that the present invention provides certain unobvious advantages and advancements over the prior art. In particular, the inventors have recognized a need for improvements in test element analysis systems with contact surfaces coated with hard material.

Although the present invention is not limited to specific advantages or functionality, it is noted that the present invention provides a test element analytical system that is simple to use and ensures an analyte determination that is as free of errors as possible even after a test element has been inserted many times into the evaluation instrument. In particular, the aim is to provide a contact connection for a test element analytical system which ensures a defined and reproducible transition resistance between the test element and evaluation instrument and thus an exact and reproducible signal transfer and analyte determination over the entire life time of such a system for many thousand insertions.

In accordance with one embodiment of the present invention, a test element analytical system for the analytical examination of a sample is provided comprising a test element and an evaluation instrument. The test element has at least one measuring zone and electrically conductive contact areas, the sample to be examined being brought into the measuring zone for the analytical examination. The evaluation instrument has a test element holder for positioning the test element containing the sample and a measuring device for measuring a change in the measuring zone that is characteristic for the analyte, the test element holder containing contact elements with contact areas which enable an electrical contact between the contact areas of the test element and the contact areas of the test element holder, wherein one of these contact areas has an electrically conductive hard material surface.

These and other features and advantages of the present invention will be more fully understood from the following detailed description of the invention taken together with the accompanying claims. It is noted that the scope of the claims is defined by the recitations therein and not by the specific discussion of features and advantages set forth in the present description.

BRIEF DESCRIPTION OF THE DRAWINGS

The following detailed description of the embodiments of the present invention can be best understood when read in conjunction with the following drawings, where like structure is indicated with like reference numerals and in which.

Figure 1:
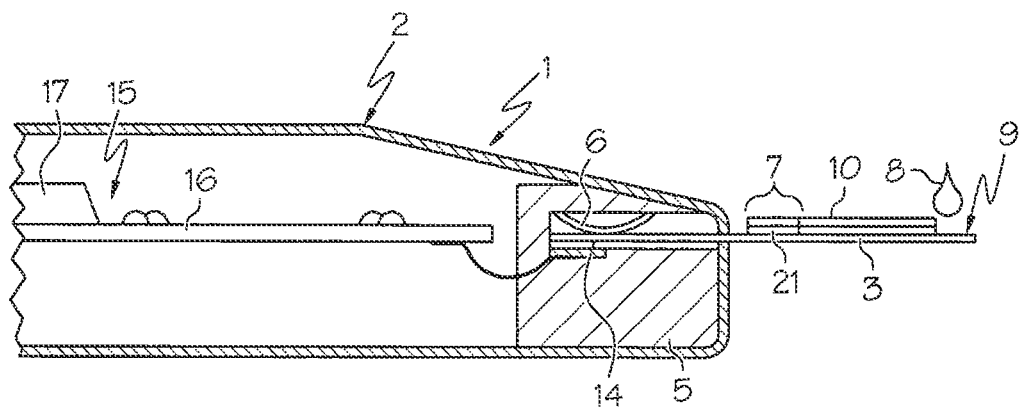
FIG. 1 shows a partial sectional view of a test element analytical system according to an embodiment of the present invention.

Skilled artisans appreciate that elements in the figures are illustrated for simplicity and clarity and have not necessarily been drawn to scale. For example, the dimensions of some of the elements in the figures may be exaggerated relative to other elements to help improve understanding of the embodiments) of the present invention.

The numbers in the figures denote:
1 analytical system
2 evaluation instrument
3 test element
4 electrodes
5 test element holder
6 spring element
7 measuring zone
8 liquid drop of sample
9 sample application zone
10 transport zone
11 contact area of the test element
12 contact area of the contact element
13 conductor path
14 contact element
15 measuring and evaluation electronics
16 printed circuit board
17 integrated circuit
18 base material
19 intermediate layer
20 hard material layer
21 reagent layer

DETAILED DESCRIPTION OF THE INVENTION

The invention concerns a test element analytical system for the analytical examination of a sample in particular a body fluid at least comprising a test element with one or more measuring zones and contact areas located on the test element in particular electrodes or conductor paths, the sample to be examined being brought into the measuring zone in order to carry out an analysis in order to determine a measurable variable that is characteristic for the analysis, and an evaluation instrument with a test element holder to position the test element in a measuring position and a measuring device for measuring the characteristic change where the test element holder contains contact elements with contact areas which enable an electrical contact between the contact areas of the test element and the contact areas of the test element holder, characterized in that one of these contact areas is provided with an electrically conductive hard material surface. The inventive solution in particular comprises coating a contact area of the contact connection of a test element analytical instrument with an electrical conductive hard material.

The hard material surface of an element involved in the contact connection can be such that the entire element or part of this element consists of a hard material. Since pure hard material elements often have disadvantageous mechanical and chemical properties such as brittleness, poor elastic properties or even a relatively high electrical resistance especially when the hard material has a large thickness, the hard material surface is formed in a typical embodiment by coating a base material with an electrically conductive hard material. Hence in the present invention mainly thin hard material layers are described as contact areas. The properties and fields of application described in the present invention for these hard material layers can, however, also be applied to surfaces of elements which are composed wholly or in large parts of a hard material.

It surprisingly turned out that a defined and reproducible electrical contact between the test element and evaluation instrument is ensured especially even after many insertions by coating a contact area with an electrically conductive hard material. Surprisingly the coating of a contact area with an electrically conductive hard material exhibits considerably improved contact properties compared to the previously widely used contact connections which often have contact areas made of a noble metal on both sides or in which both contact areas are often coated with materials which are intended to reduce the wear of the contact areas. The former are often used for test elements which are intended to be used only once and the latter are used mainly for contact connections which are designed for continual contacting operations and/or are subject to high mechanical stress.

In contrast to metallic contact areas, contact areas which are provided with a surface of hard material have the following special advantages: They have ceramic properties like a very high hardness, they are very resistant to chemical effects, they have very good sliding properties over surfaces and have only extremely low wear, deposition and abrasion loss rates. Their high degree of wettability by metallic melts ensures that the layer of hard material and underlying metal layer cohere very strongly and are thus also very suitable for applications in composite systems. In addition metallic hard materials have very good electrical properties such as a high electrical conductivity so that they are very suitable as a surface material for electrical contact connections especially in test element analytical systems.

Hard materials in the sense of the present application are understood as materials which, due to their specific binding properties, are very hard and in particular have a Vickers hardness of greater than about 1000 kp/mm$^2$. The melting point of hard materials is usually above 2000° C., their chemical and mechanical stability is good and comparable to that of ceramic materials. The term of hard materials in the sense of the present application especially encompasses metallic hard materials. These are characterized by metallic properties such as shine and electrical conductivity. Metallic hard materials include in particular carbides, borides, nitrides and silicides, high-melting metals such as chromium, zirconium, titanium, tantalum, tungsten or molybdenum including mixed crystals and complex compounds thereof. In particular they also include modifications of the above-mentioned hard materials which contain further additions of other metallic or non-metallic substances to further optimize their physical and chemical properties which are often in low concentrations. Such more complex hard material compounds can in particular be aluminum nitrides, carbonitrides or carbide carbons of the above-mentioned metals. This definition of hard materials largely corresponds to the definition from the "Römpp Lexikon Chemie" (Thieme Publisher Stuttgart, 10th Edition 1996). The hard material used for coating within the scope of the present invention should have electrically conducting properties to ensure a low transition resistance between the contact areas of the test element holder of the evaluation instrument and the test element which enables an exact and reproducible signal transfer. In particular the transition resistance between the contact areas of the test element and the contact areas of the test element holder can be less than about 50 Ohm.

Surprisingly it turned out that such metallic hard materials can be used especially as advantageous surface materials according to the invention since they have additional advantageous properties for use in contact elements of test element analyzers such as a high mechanical hardness, high chemical stability, very good gliding properties and a low degree of wear.

Particularly typical hard material surface materials of contact areas within the scope of the present invention are metallic nitrides and in particular titanium nitride, titanium aluminum nitride, chromium nitride or zirconium nitride.

According to an embodiment of the present invention one of the contact areas of the test element or of the contact element of the test element holder of the evaluation instrument is provided with an electrically conductive hard material surface. Contact areas are understood within the scope of the present invention as electrically conductive structures of the test element or of the contact element which are directly contacted in order to make an electrical contact between the test element and evaluation instrument. In the case of the test carrier they are typically electrodes and conductor paths mounted thereon and especially areas of these electrodes or conductor paths which have a formed, for example flat, structure to make the electrical contact. The contact areas of the contact element can also be shaped, for example as flat elements, to generate the largest possible contact areas and thus a very secure contact and low transition resistance. These contact areas can also have curved shapes so that the test element can be inserted as simply and gently as possible for example in the case of spring or plug-in contacts.

In a typical embodiment of a test element analytical system according to the invention the contact areas of the contact elements of the test element holder are provided with an electrically conductive hard material surface.

The contact elements which are components of the test element holder of the evaluation instrument can have a very wide variety of designs. They can for example be designed as sliding contacts, roller contacts, plug-in contacts, spring contacts, clip contacts or zero force contacts. The inventive design of the contact areas can be particularly advantageous for contact reliability especially for types of contact elements such as plug-in contacts, spring contacts and clip contacts in which the contact areas of the two elements involved in the contact connection are moved passed one another while being in direct contact until their final position is reached. Particularly typical embodiments of contact elements are plug-in contacts, spring contacts and clip contacts. A wide variety of possible embodiments of such contact elements are described in U.S. Pat. No. 6,029,344, for example.

If the hard material surface is formed as a coating, the base material of the contact elements under the hard material coating can in principle be any electrically conductive material. Metals and metal alloys which are particularly suitable for this are those which, in addition to a high electrical conductivity, additionally have a high chemical and mechanical stability. Base materials of plug-in connections that are typically used are copper alloys such as CuZn or CuSn alloys or low-alloy copper materials such as CuAg, CuCrSiTi or CuMg. In the case of spring contact elements the base materials should also have elastic properties.

A coating of hard material can in principle be applied to the base material using a variety of coating processes known to a person skilled in the art. Such processes are for example processes in which substances are deposited on surfaces from liquid solutions, electrochemical metallization or galvanizing processes, non-electro-chemical metallization processes, chemical deposition processes such as chemical vapor deposition (CVD), physical deposition processes such as physical vapor deposition (PVD) especially by evaporation processes, sputtering processes or laser ablation processes or processes which are based on the decomposition of solid, liquid or gaseous substances. PVD sputtering processes can be particularly typically used for hard material coating.

When applying a layer of hard material to the base material of the contact element, it may be advantageous to firstly apply one or more intermediate layers, in particular germ or protective layers, to the base material and subsequently apply the hard material layer to these layers. Application of such intermediate layers can in particular result in a good adhesion and a durable bonding between the different materials. Thus, for example, galvanic methods can be firstly used to apply layers to the base material which generate a particularly suitable surface for the subsequent hard material coating. Furthermore, it is also possible to apply protective layers which can protect the underlying base material from chemical and/or physical damage such as corrosion when the hard material surface is damaged. In addition, the electrical properties of the contact element such as the transition resistance can be influenced by a suitable selection of materials for such intermediate layers. Such intermediate layers can for example be produced by applying particles made of a suitable material. Alternatively, in order to obtain a good and durable bond between the base material and hard material layer it is also possible to provide an additional intermediate layer where the surface of the base material of the contact element is treated before coating in such a manner that it has improved coating properties.

The thickness and composition of the hard material layer can be influenced by a suitable choice of the coating process and its process parameters such as temperature, evaporation rate, composition of the sputter target or duration of the coating process. Surprisingly it turned out that particularly very thin layers of metallic hard materials have very good mechanical properties especially a high hardness and good sliding properties but, on the other hand, also have good electrical properties and in particular a low electrical resistance. The hard materials that have previously been used for coating surfaces are usually applied to the base material in much larger layer thicknesses. Thus DE 102 22 271 A1 describes layer thicknesses of the coating layer of 10 μm to 200 μm, U.S. Pat. No. 6,029,344 describes layer thicknesses of the coating layer between ca. 6 μm and 125 μm.

In contrast very thin hard material layers of metallic nitrides have turned out to be particularly typical within the scope of the present invention. In this connection layers of titanium nitride, titanium aluminum nitride, chromium nitride or zirconium nitride are particularly typical, layers of titanium aluminum nitride or chromium nitride are more typical. These layers typically have a layer thickness of less than about 2 μm, more typically of less than about 1 μm, and even more typically of less than about 500 nm.

Surprisingly it turned out that the advantageous effects of an electrically conductive hard material surface as a component of an electrical contact connection can be further improved especially with regard to a very secure and reproducible contact even after many contacting processes, when the properties of the second contact area are adapted to the properties of the hard material surface of the first contact area.

It turned out that there is a large increase in the transition resistance between the test element and evaluation instrument especially after several insertions in the case of contact connections in which both contact areas have noble metal surfaces which is for example caused by deposits of material on the contact areas, or it may even be no longer possible to make an electrical contact. Such noble metal-noble metal contact connections are widely used in prior test element analytical systems. The use of contact connections with noble metal-noble metal contact areas in test element analyzers is thus only of limited suitability especially with regard to the high accuracy and reproducibility of the analyte determination.

The use of a hard material surface as a contact area in an electrical contact connection can avoid the disadvantages of such contact connections with noble metal-noble metal contact areas.

With regard to a high and reproducible contact reliability, especially after many contacting processes, it has surprisingly turned out that the contact reliability can be further improved when only one contact area is provided with a hard material surface and the second contact area is composed of another material.

In particular it has turned out to be particularly advantageous when the contact area opposite to the contact area provided with a hard material surface consists of a material which has a lower hardness than the material of the hard material surface of the other contact area. Metals are typically suitable for this and especially noble metals such as gold, palladium or platinum. Such materials are already widely used for contact areas especially of electrodes and conductor paths on test elements. Consequently it is in many cases sufficient to provide the evaluation instrument with contact elements having hard material surfaces according to the invention, in which such conventional test elements can then be inserted. The combination of a contact area with a hard material surface and a contact area made of a material which has a lower hardness than the material of the hard material surface enables a high reproducibility of the transition resistance between the test element and evaluation instrument to be achieved. Surprisingly in endurance tests in which in each case a new test element with contact elements made of gold was inserted several hundred or even thousands of times into a contact element according to an embodiment of the invention with chromium nitride-coated or titanium aluminum nitride-coated contact areas, it was observed that the transition resistances remained stable and were below 50 Ohm even after many insertions. Microscopic observation of the surface of the test element showed that, in contrast to contact connections with noble metal-noble metal contact areas, although the contact area of the test element was deformed, large deposits of material or changes of the layer thicknesses were not observed. In particular, a continuous metal layer is preserved on the electrodes and conductor paths.

The smallest possible damage to the contact area is of decisive importance for an exact and reproducible analyte determination especially with very thin layer thicknesses of such electrodes, conductor paths or contact areas. Such test elements are for example electrochemical test strips which have very thin metal layers, for example noble metal contacts with layer thicknesses in the nanometer to micrometer range on an electrically insulating plastic foil. Such metal layers can for example be produced on such supports by lithographic methods (layer thicknesses typically 10-100 μm) or laser ablation (layer thicknesses typically 10-100 nm). In the case of such very thin electrically conductive metal layers on insulating and elastic surfaces, a slight erosion of this layer can considerably increase the transition resistance or in an extreme case completely interrupt the electrical contact. The inventive hard material surfaces of the opposing contact areas result in much less damage to such metal layers thus enabling an exact and reproducible analyte determination in test element analyzers.

There are still technical problems associated with coating the contact areas of conventional test elements with hard materials since for example the application of a relatively brittle hard material layer to an elastic and flexible plastic foil of a test element has an adverse effect on the mechanical properties of the test element with regard to a simple and error-free handling or the process conditions of the coating process are unsuitable for conventional test elements. Hence, in a particularly typical embodiment the contact areas of the test element are made of a soft material and the contact areas of the contact element of the evaluation instrument are provided with a hard material surface since the mechanical requirements are much more suitable for a hard material coating in the case of such rigid plug-in connections.

In addition to the typical embodiment of a combination of a hard material-coated contact area of the evaluation instrument and a contact area of the test element which consists of a material of a lower hardness and especially of a noble metal, all other combinations of a hard material surface and a second contact area comprising a material of lower hardness are possible. In particular the contact area of the test element can have a hard material surface and the contact area of the contact element of the evaluation instrument can have a surface made of a material of lower hardness. Such combinations have the same inventive advantages.

Test element analytical systems are typically used in analytical and medical laboratories. However, the invention is also directed towards fields of application in which the analysis is carried out by the patients themselves in order to continuously monitor their state of health (home monitoring). This is of particular medical importance for example for monitoring diabetics who have to determine the concentration of glucose in their blood several times daily or patients who take anti-coagulant drugs and therefore have to determine their coagulation status at regular intervals. For such purposes the evaluation instruments should be as light and small as possible, and be battery operated and robust. Such test element analytical systems are described for example in DE 43 05 058.

Test elements are frequently in the form of test strips which are essentially composed of an elongate support layer usually consisting of a plastic material and a measuring zone with a detection layer containing the detection reagents and possibly other auxiliary layers such as filtration layers. In addition test elements can contain other structural elements, for example dosing and transport devices for the sample such as channels or fleeces, positioning devices such as cut-outs to ensure an exact positioning of the test element and thus an exact measurement in the evaluation instrument or coding elements for example in the form of a bar code or an electronic component which are used to transfer specific parameters of the test element such as calibration data or batch information to the evaluation instrument.

Test elements usually contain reagents in the measuring zone whose reaction with the sample and in particular with the analytes contained in the sample result in a characteristic and measurable change of the test element which can be determined by the evaluation instrument which is part of the system. The measuring zone can optionally contain other auxiliary substances. The measuring zone can also contain only parts of the reagents or auxiliary substances. In other cases it is possible that the detection reactions to determine the analyte do not occur directly in the measuring zone but rather the reagent mixture is only transferred to the measuring zone for measurement after the detection reactions are completed. One skilled in the art of analytical test elements or diagnostic test carriers is very familiar with suitable reagents and auxiliary agents for carrying out analyte-specific detection reactions. In the case of analytes that are detected analytically, the measuring zone can for example contain enzymes, enzyme substrates, indicators, buffer salts, inert fillers and such like. In addition to detection reactions which result in color changes, a person skilled in the art also knows other detection principles which can be realized with the described test element such as electrochemical sensors or chemical, biochemical, molecular biological, immunological, physical, fluorimetric or spectroscopic detection methods. The subject matter of the present invention can be used in all these detection methods. This applies particularly to electrochemical analytical methods in which, as a result of an analyte-specific detection reaction, a change in the measuring zone occurs that can be measured electrochemically usually as a voltage or current flow.

In addition to such analytical systems that use reagents, the subject matter of the present invention can also be used in reagent-free analytical systems in which, after the test element has been contacted with the sample, a characteristic property of the sample (for example its ion composition by means of ion selective electrodes) is measured directly without further reagents. The invention can also be fundamentally used for such analytical systems.

The test elements of the present invention additionally contain contact areas that are electrically conductive and by means of which an electrical contact can be made between the test element and the evaluation instrument. In the case of electro-chemical analytical methods, conductor paths and electrodes are mounted on the test element which can be used to determine electrochemical changes in the sample and also to apply external voltages and/or currents to the sample to be examined. The electrochemical analyses on the test element can occur in particular in the measuring zone between designed electrodes while the electrical measuring signals that are emitted by them or the actuating signals directed towards them are measured or applied via the conductor paths. These conductor paths can contain designed flat areas which form contact areas that can be used to make an electrical contact between the test element and evaluation instrument. The conductor paths and contact areas usually consist of noble metals. Test elements which do not use electrochemical analytical methods can also have electrically conductive contact areas. For example, it may be advantageous to mount electronic components on a test element which are used to store specific parameters of the test element such as calibration data or batch data and transfer them to the evaluation instrument. For this purpose these specific data are stored on the test element in electronic components or circuits. When the test element is introduced into the evaluation instrument, these data can be read and processed by reading electronics of the evaluation instrument. However, for this it is necessary to electrically contact the test element which is why again the aforementioned electrically conductive contact areas of the test element are indispensable.

In accordance with an embodiment of the present invention, the evaluation instrument contains a test element holder in order to position a test element in a measuring position for carrying out the measurement. This test element holder additionally contains the previously described contact elements with contact areas. In order to determine the analyte, the test element is placed in an evaluation instrument which determines the characteristic change of the test element that is caused by the analyte and provides it in the form of a measured value for display or further processing. The analyte can be determined with a variety of detection methods known to a person skilled in the field of instrument analytics. In particular optical and electrochemical detection methods can be used. Optical methods for example encompass the determination of characteristic changes in the measuring zone by measuring absorption, transmission, circular dichroism, optical rotation dispersion, refractometry or fluorescence. Electrochemical methods can in particular be based on the determination of characteristic changes in charge, potential or current in the measuring zone.

Analytes that can be determined by the method according to an embodiment of the present invention or by the corresponding devices are, in the sense of the present application, all particles that are of interest in analytics in particular in clinical diagnostics. In particular the term "analyte" encompasses atoms, ions, molecules and macromolecules, in particular biological macromolecules such as nucleic acids, peptides and proteins, lipids, metabolites, cells and cell fragments.

In the sense of the present application the sample used for the analytical examination is understood as an unchanged medium containing the analyte as well as an already changed medium containing the analyte or substances derived therefrom. The change in the original medium can in particular be carried out in order to lyse the sample, to process the analyte or to carry out detection reactions. Typical samples are liquids. Liquids can be pure liquids and homogeneous or heterogeneous mixtures such as dispersions, emulsions or suspensions. In particular, the liquids can contain atoms, ions, molecules and macromolecules, in particular biological macromolecules such as nucleic acids, peptides and proteins, lipids, metabolites or also biological cells or cell fragments. Typical liquids to be examined are body fluids such as blood, plasma, serum, urine, cerebrospinal fluid, lachrymal fluid, cell suspensions, cell supernatants, cell extracts, tissue lysates or such like. Liquids can, however, also be calibration solutions, reference solutions, reagent solutions or solutions containing standardized analyte concentrations, so-called standards.

In the present application an analytical examination or determination of analytes is understood as a qualitative as well as a quantitative detection of the analyte. In particular, it is understood as a determination of the concentration or amount of the respective analyte where the sole determination of the absence or presence of the analyte is also regarded as an analytical examination.

The invention is further elucidated in the following on the basis of the figures and embodiment examples. The described properties and characteristics can be used individually or in combination in order to create typical embodiments of the invention.

The test element analytical system 1 shown in FIG. 1 consists of an evaluation instrument 2 and a test element 3. The evaluation instrument 2 has a test element holder 5 which positions a test element 3 in the measuring position shown in FIG. 1. The test element 3 is fixed in the measuring position by suitable means for example by a spring element 6.

In order to carry out a measurement, sample liquid is brought into the measuring zone 7 of the test element 3. In the embodiment shown this occurs by applying a drop of liquid 8 to the sample application zone 9 provided at the end of the test element 3 and transporting it from this position through a transport zone 10, for example a capillary gap, to the measuring zone 7. A reagent layer 21 is located in the measuring zone 7 which is dissolved by the sample liquid and reacts with its components.

The reaction results in a detectable change in the measuring zone 7. In the case of an electrochemical test element the measured electrical quantity is determined by means of the electrodes 4 shown in FIG. 2 that are provided in the measuring zone 7. In the measuring position an electrical contact is made between the test element 3 and the contact element 14 of the test element holder 5 (FIG. 1). The contact element 14 is connected to measuring and evaluation electronics 15 which are highly integrated in order to achieve a very compact construction and high degree of reliability. In the case shown they are essentially composed of a printed circuit board 16 and an integrated circuit 17. To this extent the analytical system has a conventional construction and needs no further explanation.

Figure 2:
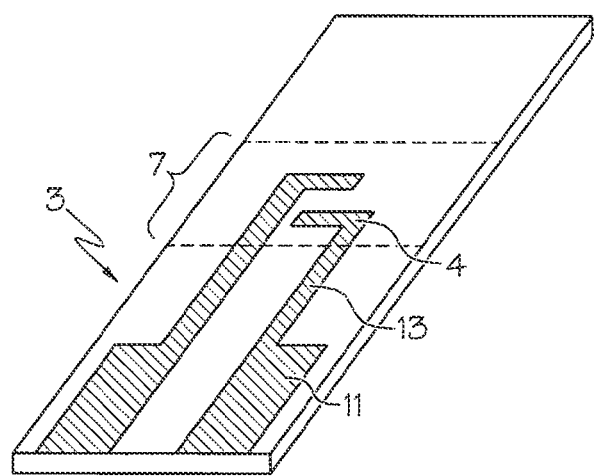
FIG. 2 shows an exemplary view of a test element for electrochemical analytical methods.

FIG. 2 shows a partial view of an exemplary test element 3 for electrochemical analytical methods. An analyte-specific change is detected as part of the analyte determination within the measuring zone 7. In the case shown of an electrochemical test element a measured electrical quantity is measured by means of electrodes 4 provided in the measuring zone 7. The electrical signal is passed onto the contact areas 11 via the conductor paths 13. These contact areas 11 make direct contact with the contact areas of the contact element 12 (see FIG. 3) when the test element 3 is plugged into the test element holder 5 and thus make an electrical contact between test element 3 and evaluation instrument 2. The test element that is shown here is only an exemplary and minimalized embodiment of a test strip. Test elements with other arrangements of electrodes and conductor paths and with several electrodes, for example reference electrodes, and additional structures such as sample application and transport zones or reaction areas can also be used within the scope of the present invention.

Figure 3:
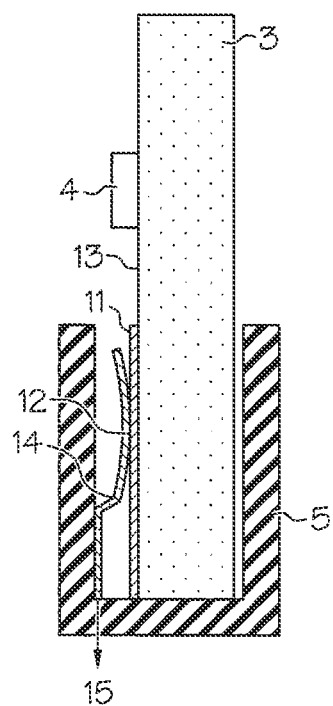
FIG. 3 shows a detailed view of a contact element according to an embodiment of the present invention.

FIG. 3 shows a detailed view of a contact element 14 according to an embodiment of the present invention. The test element 3 is introduced into the test element holder 5 by insertion. Electrical contact is made between the contact areas of the contact element 12 and the contact area of the test element 11. In this case the contact element 14 is designed such that it has elastic properties and thus exerts a defined contact pressure on the test element 3. This is exhibited by a particularly typical embodiment in which the contact element 14 ensures the electrical contacting as well as the positioning and fixing of the test element 3. In contrast, the functions of electrical contacting and positioning/fixing are divided between two different components in the embodiments illustrated in FIG. 1, namely the spring element 6 and the contact element 14.

Figure 4:
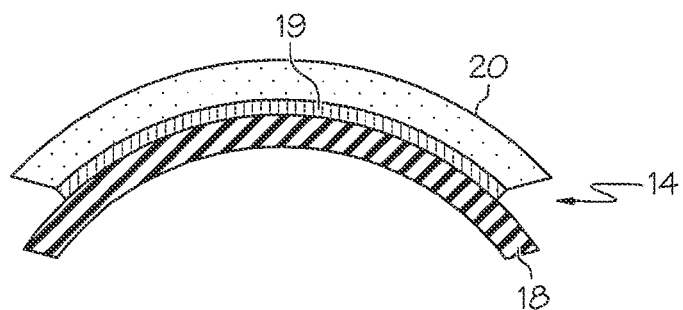
FIG. 4 shows a detailed view of a cross-section of a contact element coated with a hard material in the region of the contact area.

FIG. 4 shows a detailed view of a cross-section of a contact element coated with a hard material in the region of the contact area in accordance with an embodiment of the present invention. The hard material layer 20 is in this case applied to the base material 18 of the contact element and an intermediate layer 19 is present in this case between the two layers which in particular can be designed as a bonding or protective layer. The hard material layer 20 functionally corresponds to the contact area of the contact element 12.

In order that the invention may be more readily understood, reference is made to the following examples, which are intended to illustrate the invention, but not limit the scope thereof.

EXAMPLES

For use in test element analytical systems it is important that the contact connections between the test elements and analytical instrument still guarantee defined and low transition resistances even after numerous insertions in order to ensure an exact and reproducible analyte determination by the test element analyzer.

Example 1

Contact Elements with Chromium Nitride-Coated Contact Areas a) Microscopic Examination of the Surface In order to demonstrate the advantageous effect of hard material surfaces according to the invention as contact areas in an electrical contact connection of a test element analytical system, the contact areas of such plug-in connections were coated with chromium nitride. A 480 nm thick chromium nitride layer was applied to the contact areas of the plug-in connection using a PVD process. In each case new test elements were plugged 480 times into plug-in connections coated in this manner. These test elements had gold layers having a thickness of 50 nm as contact areas which were applied to a plastic foil. After 480 insertions the picture of damage to the contact areas of the plug-in connection as well as to the individual contact areas of the test elements were evaluated microscopically. As a comparison 480 test elements were inserted into conventional, non-hard material-coated plug-in connections with contact areas made of electropolished palladium under otherwise identical conditions and also microscopically evaluated.

The picture of damage to the contact areas of the test elements which were inserted into conventional plug-in connections having contact areas made of electropolished palladium exhibited a great amount of material erosion and deformations of the gold layer of the test elements. These were the result of the relative movement of the test element across the plug-in connection. Thus the gold layer on the contact areas and conductor paths of the test element are highly deformed by the second contact area of the plug-in connection that moves relatively across it. This deformation can be to such an extent that in some areas the gold layer is abraded down to the plastic foil due to the second contact area scratching across it. As a result the electrical contact is interrupted in these cases and hence an analyte determination is impossible.

In contrast, the picture of damage to the contact areas of the test elements which were inserted into plug-in connections according to an embodiment of the present invention whose contact areas were coated with 480 nm chromium nitride exhibited considerably less damage. Microscopic observation of the contact areas of the test element showed that the contact areas of the test element were deformed to a much lesser extent than with the plug-in connections that were not coated with a hard material. In particular, larger material erosions or changes in the layer thicknesses were not observed and the gold layer of the contact areas and conductor paths remained in all cases as a continuous layer. The microscopic picture of damage showed a more uniform deformation of the gold layer in the form of a flat channel with relatively constant and small depths without material being strongly or even completely eroded at particular sites.

The microscopic picture of damage of conventional contact areas of contact elements of plug-in connections which were not coated with a hard material after 480 insertions was also much worse than the microscopic picture of damage of corresponding contact areas with a hard material surface according to the embodiment of the invention consisting of 480 nm chromium nitride.

The non-hard material-coated contact areas of the contact elements of the control plug-in connections exhibited considerable wear of the metal layer when observed under the microscope which resulted in a complete abrasion of the metal layer at some sites. In some cases deposits of surface materials of the inserted test elements were also observed on the contact areas of the plug-in connections.

In contrast, the chromium nitride-coated contact areas of the contact elements according to an embodiment of the present invention exhibited no significant signs of wear even after such frequent insertions. In particular, the chromium nitride layer was observed to have an intact and continuous surface and there was a reduced deposition of the electrode material of the test strip.

b) Electrical Transition Resistances

When the electrical transition resistances were measured between the test element and contact element of the plug-in connection it was observed that, especially after many insertions, the contact elements coated with a hard material enable considerably more reproducible electrical contact connections that are less susceptible to interference than conventional contact elements without such a hard material surface. For this purpose in each case 480 new test elements of the type described above which had a 50 nm thick gold layer as the electrode material were either inserted into plug-in connections whose contact areas were coated with 480 nm chromium nitride or into plug-in connections with non-hard material coated contact areas made of electropolished palladium (controls) and in each case the transition resistances were determined between 8 electrode areas of a test element and the plug-in connection so that in each case 3840 values of transition resistances were obtained for hard material-coated contact areas and non-hard material-coated control contact areas.

Figure 5A:
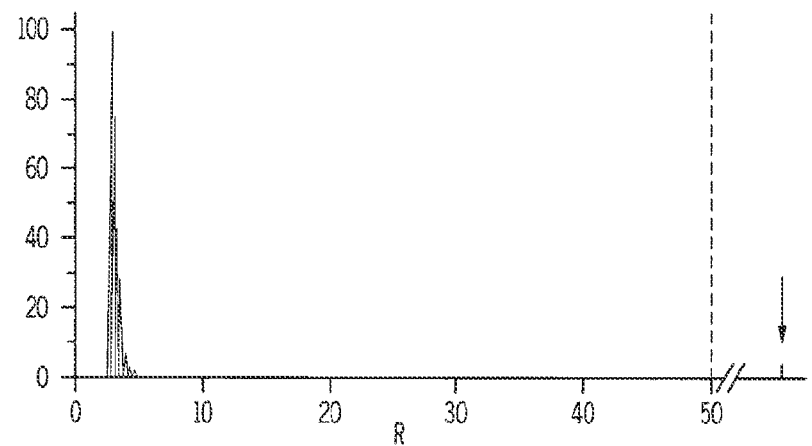
FIGS. 5a-5c show frequency distributions of experimentally determined transition resistances between contact elements with non-hard material coated contact areas of electropolished palladium (FIG. 5a), between contact elements with chromium nitride-coated contact areas (FIG. 5b), or contact elements with titanium aluminum nitride-coated contact areas (FIG. 5c) and in each case new test elements with contact areas consisting of 50 nm gold.

FIG. 5a shows a frequency distribution of the transition resistances determined in this manner for contact elements with non-hard material-coated contact areas made of electropolished palladium. The measured transition resistance R is plotted on the abscissa in 0.1 Ohm ranges and the frequency f of the measured transition resistances normalized to the highest frequency value (=100) are plotted on the ordinate.

This shows that most of the transition resistances in these controls are in the low value range between 0 and 10 Ohm but a not inconsiderable number of measured transition resistances reach an "infinite" magnitude. Such transition resistances measured as "infinite" mean that there is no electrical contact between the respective contact element of the plug-in connection and the contact area of the test element and no resistance can be measured. These values are marked by the arrow on the right side of FIG. 5a. The evaluation of the individually measured transition resistances showed that 32 of the measured transition resistances were larger than 50 Ohm. A transition value of 50 Ohm is regarded as a threshold value in test element analytical systems constructed in this manner below which a measurement can still be regarded as reliable. 16 of the examined 480 test elements, however, had at least one transition resistance value above 50 Ohm. This resulted in a high error rate of 3.3% of the measured test elements so that such contact elements are of only limited suitability for a permanent and reproducible use in test element analytical systems.

Figure 5B:
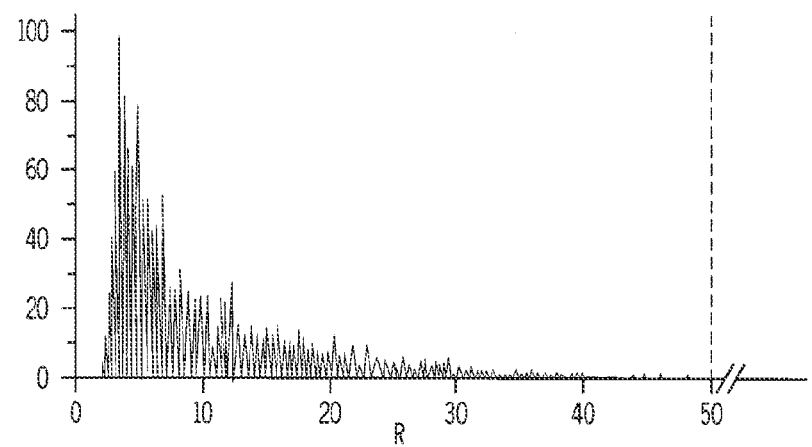

FIG. 5b shows a frequency distribution of the measured transition resistances for contact elements according to an embodiment of the invention which were hard material-coated with 480 nm chromium nitride.

It can be clearly seen that no values larger than 50 Ohm were observed in the determination of the 3840 transition resistances. Although more resistance values were between 10 and 50 Ohm, none of the measured 3840 values were above the threshold value of 50 Ohm and none of the transition resistance values were "infinite" as with the non-hard material-coated contact areas. Thus, such contact connections can be used to transfer electrical signals reproducibly and exactly for many plug-in operations. The use of such contact connections according to the invention in test element analyzers thus has the advantage that in such systems reproducible and exact analyte determinations can be carried out especially even after numerous insertions.

Example 2

Contact Elements with Titanium Nitride-Coated Contact Areas

Analogous experiments were carried out with plug-in connections with contact elements whose contact areas had a hard material surface according to an embodiment of the invention consisting of 120 nm titanium aluminum nitride which was also applied by means of a PVD process.

a) Microscopic Examination of the Surface

Also in this case it turned out that a hard material-coating of the contact areas of the plug-in connection with titanium aluminum nitride according to the instant embodiment considerably improves the picture of damage to the contact areas of the test elements. Microscopic observation of the respective contact areas of the test element showed that the contact area of the test element was deformed but to a much lesser extent than with the controls that were not coated with a hard material. In particular, larger material erosions or changes in the layer thicknesses were not observed and the gold layer of the contact areas and conductor paths remained as a continuous layer. The microscopic picture of damage showed, similar to a chromium nitride-coated contact area, a more uniform deformation of the gold layer in the form of a flat channel with a relatively constant and small depth without material being strongly or even completely eroded at particular sites.

Also the damage to the titanium aluminum nitride coating itself was much less after 480 insertions than with the non-hard material coated control plug-in connections. The titanium aluminum nitride-coated contact areas of the plug-in connections according to an embodiment of the invention exhibited no significant signs of wear or deposits even after frequent insertions. In particular, the surface of the titanium nitride layer was observed to still be intact and continuous.

b) Electrical Transition Resistances

In the measurement of transition resistances, like the measurement in example 1b), it turned out that contact areas of plug-in connections coated with titanium aluminum nitride enable considerably more reproducible electrical contact connections between the plug-in connection and test element that are considerably less susceptible to interference than conventional plug-in connections without such a hard material surface. A particular advantage of this embodiment is that in addition to a very high contact reliability (no values above 50 Ohm) compared to the chromium nitride-coated contact areas from example 1, the values of the measured transition resistances are even considerably lower.

Figure 5C:
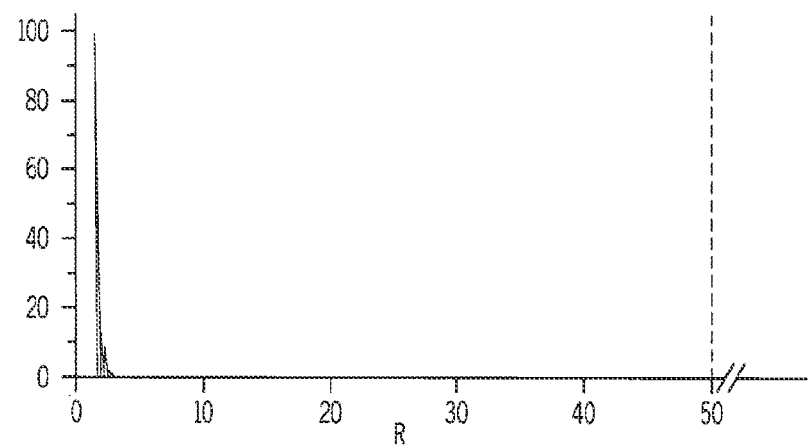

FIG. 5c shows a frequency distribution of the measured transition resistances for contact elements according to an embodiment of the invention with contact areas coated with a hard material comprising 120 nm titanium aluminum nitride.

The determination of transition resistances clearly showed that no values were observed that are larger than 50 Ohm. Also almost all measured resistance values were between 1 and 3 Ohm and thus even considerably lower than with the non-hard material-coated contact areas of example 1 (FIG. 5a). Thus such contact connections can be used to transfer electrical signals reproducibly and exactly for many plug-in operations. The use of such contact connections according to the invention in test element analyzers thus has the advantage that in such systems reproducible and exact analyte determinations can be carried out especially even after numerous insertions. The very low transition resistances in the case of contact elements with titanium aluminum nitride-coated contact areas have the additional advantage that the actual measurement signal is hardly affected by the transition resistance and thus it is possible to carry out particularly exact analyte determinations even with low measurement signals.

Example 3

Change in the Transition Resistances from Example 1 and 2 after Numerous Plug-In Processes For reproducible use in test element analytical systems over a long time period and for many measurement cycles it is also important that the transition resistances are as constant as possible and do not exhibit an extreme running-in or wear behavior which is characterized by initially high and then decreasing resistance values or initially low and then increasing resistance values.

Control plug-in connections with contact areas made of electropolished palladium exhibited scattered contact failures characterized by "infinite" resistance values over the 480 insertions of a new test element in each case over the entire time period. Such randomly scattered contact failures are disadvantageous especially for the reproducibility of the measurement result since a measurement error must always be expected with a certain probability.

Plug-in connections with contact areas which were coated with 480 nm chromium nitride exhibited an increase in the transition resistances with an increasing number of insertions. In such test systems it can therefore be advantageous to replace the contact elements coated with the hard material after a certain number of measurements in order to ensure a constant high accuracy of measurement. For this reason the present invention also encompasses such hard material-coated contact elements and contact connections as well as evaluation instruments which contain such contact elements and contact connections coated with the hard material.

Plug-in connections with contact areas which were coated with 120 nm titanium aluminum nitride initially exhibited higher transition resistances which decreased to a very low resistance level with an increasing number of insertions. This observation shows that, in contrast to a chromium nitride coating, very reproducible and low transition resistances can be achieved especially even after many insertions by use of a titanium aluminum nitride coating and such coatings of contact areas are especially suitable for test element analytical systems which should enable exact analyte determinations over a very long period of use and very many measurements.

This shows that it is also possible to adapt the test element analytical system to the requirements of the respective field of application especially with regard to the life-time and exactness of the analyte determination by selection of the material for the hard material surface.

It is noted that terms like "preferably", "commonly", and "typically" are not utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention.

For the purposes of describing and defining the present invention it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

Having described the invention in detail and by reference to specific embodiments thereof, it will be apparent that modifications and variations are possible without deparing from the scope of the invention defined in the appended claims. More specifically, although some aspects of the present invention are identified herein as preferred or particularly advantageous, it is contemplated that the present invention is not necessarily limited to these preferred aspects of the invention.

What is claimed is:

1. A test element analytical system for the analytical examination of a sample comprising:
   a test element having at least one measuring zone and electrically conductive contact areas, the sample to be examined being brought into the measuring zone for the analytical examination, and
   an evaluation instrument having a test element holder for positioning the test element containing the sample and a measuring device for measuring a change in the measuring zone that is characteristic for an analyte, the test element holder containing contact elements with contact areas opposing the contact areas of test element which enable electrical contact between the contact areas of the test element and the contact areas of the test element holder, wherein the contact areas of the test element comprise a material having a lower hardness than an electrically conductive material surface of the contact areas of the test element holder.

2. The test element analytical system of claim 1, wherein the contact areas of the test element holder are in the form of plug-in contacts, spring contacts or clip contacts.

3. The test element analytical system of claim 1, wherein the material surface is produced by coating a base material with an electrically conductive material.

4. The test element analytical system of claim 3, wherein additional intermediate layers are present between the base material and the material surface.

5. The test element analytical system of claim 4, wherein said intermediate layers comprise bonding layers or protecting layers.

6. The test element analytical system of claim 1, wherein the electrically conductive material surface comprises a material coating having a layer thickness of less than 2 μm.

7. The test element analytical system of claim 1, wherein the electrically conductive material surface comprises a material coating having a layer thickness of less than 1 μm.

8. The test element analytical system of claim 1, wherein the electrically conductive material surface comprises a material coating having a layer thickness of less than 500 nm.

9. The test element analytical system of claim 1, wherein the electrical transition resistance between the contact areas of the test element and the contact areas of the test element holder is less than 50 Ohm.

10. The test element analytical system of claim 1, wherein the sample is a body fluid.

11. The test element analytical system of claim 1, wherein the electrically conductive contact areas of the test element comprise electrodes and/or conductor paths.

12. The system of claim 1, wherein the system is configured so that the electrical contact is established by moving the contact areas of the test element in relation to the contact areas of the holder while in direct contact until a final position is reached.

* * * * *